(12) United States Patent
Murad et al.

(10) Patent No.: US 12,268,599 B2
(45) Date of Patent: Apr. 8, 2025

(54) DELIVERY SYSTEMS FOR PROSTHETIC HEART VALVE

(71) Applicant: Edwards Lifesciences Corporation, Irvine, CA (US)

(72) Inventors: Michael C. Murad, Lake Mathews, CA (US); Michael R. Bialas, Lake Forest, CA (US)

(73) Assignee: EDWARDS LIFESCIENCES CORPORATION, Irvine, CA (US)

(*) Notice: Subject to any disclaimer, the term of this patent is extended or adjusted under 35 U.S.C. 154(b) by 886 days.

(21) Appl. No.: 17/341,844

(22) Filed: Jun. 8, 2021

(65) Prior Publication Data

US 2021/0290387 A1 Sep. 23, 2021

Related U.S. Application Data

(63) Continuation of application No. PCT/US2019/064479, filed on Dec. 4, 2019.

(60) Provisional application No. 62/778,159, filed on Dec. 11, 2018.

(51) Int. Cl.
*A61F 2/24* (2006.01)
*A61F 2/958* (2013.01)

(52) U.S. Cl.
CPC .......... *A61F 2/2433* (2013.01); *A61F 2/2436* (2013.01); *A61F 2/958* (2013.01); *A61F 2002/9583* (2013.01); *A61F 2250/0098* (2013.01)

(58) Field of Classification Search
CPC .................. A61F 2/2433; A61F 2/2436; A61F 2250/0098; A61F 2002/9583; A61F 2002/9586
See application file for complete search history.

(56) References Cited

U.S. PATENT DOCUMENTS

| | | | |
|---|---|---|---|
| 519,297 | A | 5/1894 | Bauer |
| 4,035,849 | A | 7/1977 | Angell et al. |
| 4,592,340 | A | 6/1986 | Boyles |
| 4,955,895 | A | 9/1990 | Sugiyama et al. |
| 4,994,077 | A | 2/1991 | Dobben |

(Continued)

FOREIGN PATENT DOCUMENTS

| | | |
|---|---|---|
| CN | 103826571 A | 5/2014 |
| DE | 19532846 A1 | 3/1997 |

(Continued)

*Primary Examiner* — Sarah W Aleman
(74) *Attorney, Agent, or Firm* — Klarquist Sparkman, LLP; Linda Allyson Nassif

(57) ABSTRACT

A delivery apparatus can include a handle, a first shaft extending from the handle and having a proximal end portion coupled to the handle and a distal end portion and a second shaft extending coaxially over the first shaft and having a proximal end portion coupled to the handle and a distal end portion. The delivery apparatus can further include a shoulder coupled to the distal end portion of the second shaft and having a flared end portion configured to abut a prosthetic valve positioned around the first shaft in a radially compressed state, an extension portion extending from the shoulder, and at least one radiopaque marker disposed on the extension portion at a location within the prosthetic valve when the prosthetic valve is in a radially compressed configuration on the first shaft.

12 Claims, 3 Drawing Sheets

(56) References Cited

U.S. PATENT DOCUMENTS

| | | | |
|---|---|---|---|
| 5,059,177 A | 10/1991 | Towne et al. | |
| 5,176,698 A | 1/1993 | Burns et al. | |
| 5,192,297 A | 3/1993 | Hull | |
| 5,266,073 A | 11/1993 | Wall | |
| 5,325,845 A | 7/1994 | Adair | |
| 5,358,496 A | 10/1994 | Ortiz et al. | |
| 5,411,552 A | 5/1995 | Andersen et al. | |
| 5,554,185 A | 9/1996 | Block et al. | |
| 5,591,195 A | 1/1997 | Taheri et al. | |
| 5,599,305 A | 2/1997 | Hermann et al. | |
| 5,632,760 A | 5/1997 | Sheiban et al. | |
| 5,639,274 A | 6/1997 | Fischell et al. | |
| 5,669,932 A * | 9/1997 | Fischell | A61F 2/958 606/198 |
| 5,728,068 A | 3/1998 | Leone et al. | |
| 5,749,890 A | 5/1998 | Shaknovich | |
| 5,782,809 A | 7/1998 | Umeno et al. | |
| 5,824,044 A | 10/1998 | Quiachon et al. | |
| 5,840,081 A | 11/1998 | Andersen et al. | |
| 5,908,405 A | 6/1999 | Imran et al. | |
| 5,916,147 A | 6/1999 | Boury | |
| 5,944,690 A | 8/1999 | Falwell et al. | |
| 5,951,569 A | 9/1999 | Tuckey et al. | |
| 5,961,536 A | 10/1999 | Mickley et al. | |
| 5,968,068 A | 10/1999 | Dehdashtian et al. | |
| 5,968,069 A * | 10/1999 | Dusbabek | A61F 2/958 604/96.01 |
| 6,019,777 A | 2/2000 | Mackenzie | |
| 6,027,510 A | 2/2000 | Alt | |
| 6,033,381 A | 3/2000 | Kontos | |
| 6,143,016 A | 11/2000 | Bleam et al. | |
| 6,162,208 A | 12/2000 | Hipps | |
| 6,168,614 B1 | 1/2001 | Andersen et al. | |
| 6,174,327 B1 | 1/2001 | Mertens et al. | |
| 6,217,585 B1 | 4/2001 | Houser et al. | |
| 6,235,050 B1 | 5/2001 | Quiachon et al. | |
| 6,251,092 B1 | 6/2001 | Qin et al. | |
| 6,379,372 B1 | 4/2002 | Dehdashtian et al. | |
| 6,383,171 B1 | 5/2002 | Gifford et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,471,672 B1 | 10/2002 | Brown et al. | |
| 6,500,147 B2 | 12/2002 | Omaleki et al. | |
| 6,514,228 B1 | 2/2003 | Hamilton et al. | |
| 6,527,979 B2 | 3/2003 | Constantz et al. | |
| 6,579,305 B1 | 6/2003 | Lashinski | |
| 6,582,462 B1 | 6/2003 | Andersen et al. | |
| 6,652,578 B2 | 11/2003 | Bailey et al. | |
| 6,730,118 B2 | 5/2004 | Spenser et al. | |
| 6,733,525 B2 | 5/2004 | Yang et al. | |
| 6,764,504 B2 | 7/2004 | Wang et al. | |
| 6,767,362 B2 | 7/2004 | Schreck | |
| 6,830,584 B1 | 12/2004 | Seguin | |
| 6,893,460 B2 | 5/2005 | Spenser et al. | |
| 6,908,481 B2 | 6/2005 | Cribier | |
| 7,011,094 B2 | 3/2006 | Rapacki et al. | |
| 7,018,406 B2 | 3/2006 | Seguin et al. | |
| 7,018,408 B2 | 3/2006 | Bailey et al. | |
| 7,137,993 B2 | 11/2006 | Acosta et al. | |
| 7,276,084 B2 | 10/2007 | Yang et al. | |
| 7,318,278 B2 | 1/2008 | Zhang et al. | |
| 7,320,702 B2 | 1/2008 | Hammersmark et al. | |
| 7,320,704 B2 | 1/2008 | Ashinski et al. | |
| 7,374,571 B2 | 5/2008 | Pease et al. | |
| 7,393,360 B2 | 7/2008 | Spenser et al. | |
| 7,435,257 B2 | 10/2008 | Lashinski et al. | |
| 7,510,575 B2 | 3/2009 | Spenser et al. | |
| 7,585,321 B2 | 9/2009 | Cribier | |
| 7,594,926 B2 | 9/2009 | Linder et al. | |
| 7,597,709 B2 | 10/2009 | Goodin | |
| 7,618,446 B2 | 11/2009 | Andersen et al. | |
| 7,780,723 B2 | 8/2010 | Taylor | |
| 7,785,366 B2 | 8/2010 | Maurer et al. | |
| 7,959,661 B2 | 6/2011 | Hijlkema et al. | |
| 8,029,556 B2 | 10/2011 | Rowe | |
| 8,167,932 B2 | 5/2012 | Bourang et al. | |
| RE43,882 E | 12/2012 | Hopkins et al. | |
| 8,449,606 B2 | 5/2013 | Eliasen et al. | |
| 8,475,523 B2 | 7/2013 | Duffy | |
| 8,568,472 B2 | 10/2013 | Marchand et al. | |
| 9,061,119 B2 | 6/2015 | Le et al. | |
| 9,119,716 B2 | 9/2015 | Lee et al. | |
| 9,795,477 B2 * | 10/2017 | Tran | A61F 2/958 |
| 2001/0002445 A1 | 5/2001 | Vesely | |
| 2001/0007082 A1 | 7/2001 | Dusbabek et al. | |
| 2002/0032481 A1 | 3/2002 | Gabbay | |
| 2002/0058995 A1 | 5/2002 | Stevens | |
| 2002/0165461 A1 | 11/2002 | Hayzelden et al. | |
| 2003/0040792 A1 | 2/2003 | Gabbay | |
| 2003/0050694 A1 | 3/2003 | Yang et al. | |
| 2003/0120341 A1 | 6/2003 | Shennib et al. | |
| 2004/0093061 A1 | 5/2004 | Acosta et al. | |
| 2004/0133263 A1 | 7/2004 | Dusbabek et al. | |
| 2004/0143197 A1 | 7/2004 | Soukup et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0015048 A1 * | 1/2005 | Chiu | A61M 25/10 604/101.04 |
| 2005/0080474 A1 | 4/2005 | Andreas et al. | |
| 2005/0096736 A1 | 5/2005 | Osse et al. | |
| 2005/0137689 A1 | 6/2005 | Salahieh et al. | |
| 2005/0149160 A1 | 7/2005 | McFerran | |
| 2005/0203614 A1 | 9/2005 | Forster et al. | |
| 2005/0203617 A1 | 9/2005 | Forster et al. | |
| 2005/0245894 A1 | 11/2005 | Zadno-Azizi | |
| 2006/0025857 A1 | 2/2006 | Bergheim et al. | |
| 2006/0282150 A1 | 12/2006 | Olson et al. | |
| 2007/0005131 A1 | 1/2007 | Taylor | |
| 2007/0073389 A1 | 3/2007 | Bolduc et al. | |
| 2007/0088431 A1 | 4/2007 | Bourang et al. | |
| 2007/0100356 A1 | 5/2007 | Lucatero et al. | |
| 2007/0112422 A1 | 5/2007 | Dehdashtian | |
| 2007/0203575 A1 | 8/2007 | Forster et al. | |
| 2007/0219612 A1 | 9/2007 | Andreas et al. | |
| 2007/0239254 A1 | 10/2007 | Chia et al. | |
| 2007/0244546 A1 | 10/2007 | Francis | |
| 2007/0265700 A1 | 11/2007 | Eliasen et al. | |
| 2008/0065011 A1 | 3/2008 | Marchand et al. | |
| 2008/0103520 A1 | 5/2008 | Selkee | |
| 2008/0125853 A1 | 5/2008 | Bailey et al. | |
| 2008/0294230 A1 | 11/2008 | Parker | |
| 2009/0024428 A1 | 1/2009 | Hudock, Jr. | |
| 2009/0069889 A1 | 3/2009 | Suri et al. | |
| 2009/0138079 A1 | 5/2009 | Tuval et al. | |
| 2009/0157175 A1 | 6/2009 | Benichou | |
| 2009/0192585 A1 | 7/2009 | Bloom et al. | |
| 2009/0228093 A1 | 9/2009 | Taylor et al. | |
| 2009/0276040 A1 | 11/2009 | Rowe et al. | |
| 2009/0281619 A1 | 11/2009 | Le et al. | |
| 2009/0299456 A1 | 12/2009 | Melsheimer | |
| 2009/0319037 A1 | 12/2009 | Rowe et al. | |
| 2010/0030318 A1 | 2/2010 | Berra | |
| 2010/0036472 A1 | 2/2010 | Papp | |
| 2010/0036473 A1 | 2/2010 | Roth | |
| 2010/0049313 A1 | 2/2010 | Alon et al. | |
| 2010/0076402 A1 | 3/2010 | Mazzone et al. | |
| 2010/0076541 A1 | 3/2010 | Kumoyama | |
| 2010/0082089 A1 | 4/2010 | Quadri et al. | |
| 2010/0094394 A1 | 4/2010 | Beach et al. | |
| 2010/0121425 A1 | 5/2010 | Shimada | |
| 2010/0145431 A1 | 6/2010 | Wu et al. | |
| 2010/0161036 A1 | 6/2010 | Pintor et al. | |
| 2010/0174363 A1 | 7/2010 | Castro | |
| 2010/0198347 A1 | 8/2010 | Zakay et al. | |
| 2010/0274344 A1 | 10/2010 | Dusbabek et al. | |
| 2011/0015729 A1 | 1/2011 | Jimenez et al. | |
| 2011/0054596 A1 | 3/2011 | Taylor | |
| 2011/0137331 A1 | 6/2011 | Walsh et al. | |
| 2011/0160846 A1 | 6/2011 | Bishop et al. | |
| 2012/0123529 A1 | 5/2012 | Levi et al. | |
| 2012/0239142 A1 | 9/2012 | Liu et al. | |
| 2013/0030519 A1 | 1/2013 | Tran et al. | |

(56) References Cited

U.S. PATENT DOCUMENTS

| | | | |
|---|---|---|---|
| 2013/0030520 A1* | 1/2013 | Lee | A61F 2/2433 623/2.11 |
| 2013/0317598 A1 | 11/2013 | Rowe et al. | |
| 2014/0012368 A1* | 1/2014 | Sugimoto | A61B 17/0057 623/2.11 |
| 2014/0296962 A1 | 10/2014 | Cartledge et al. | |
| 2017/0065415 A1 | 3/2017 | Rupp et al. | |
| 2018/0153689 A1 | 6/2018 | Maimon et al. | |
| 2018/0344456 A1 | 12/2018 | Barash et al. | |

FOREIGN PATENT DOCUMENTS

| | | |
|---|---|---|
| DE | 19907646 A1 | 8/2000 |
| EP | 0592410 B1 | 10/1995 |
| EP | 0850607 A1 | 7/1998 |
| FR | 2815844 A1 | 5/2002 |
| WO | 9117720 A1 | 11/1991 |
| WO | 9829057 A1 | 7/1998 |
| WO | 9912483 A1 | 3/1999 |
| WO | 0149213 A2 | 7/2001 |
| WO | 0154625 A1 | 8/2001 |
| WO | 0176510 A2 | 10/2001 |
| WO | 0222054 | 3/2002 |
| WO | 0236048 A1 | 5/2002 |
| WO | 0247575 A2 | 6/2002 |
| WO | 02060352 | 8/2002 |
| WO | 03030776 A2 | 4/2003 |
| WO | 03047468 | 6/2003 |
| WO | 2004019825 A1 | 3/2004 |
| WO | 2005084595 A1 | 9/2005 |
| WO | 2006032051 A2 | 3/2006 |
| WO | 2006111391 A1 | 10/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2010121076 A2 | 10/2010 |

* cited by examiner

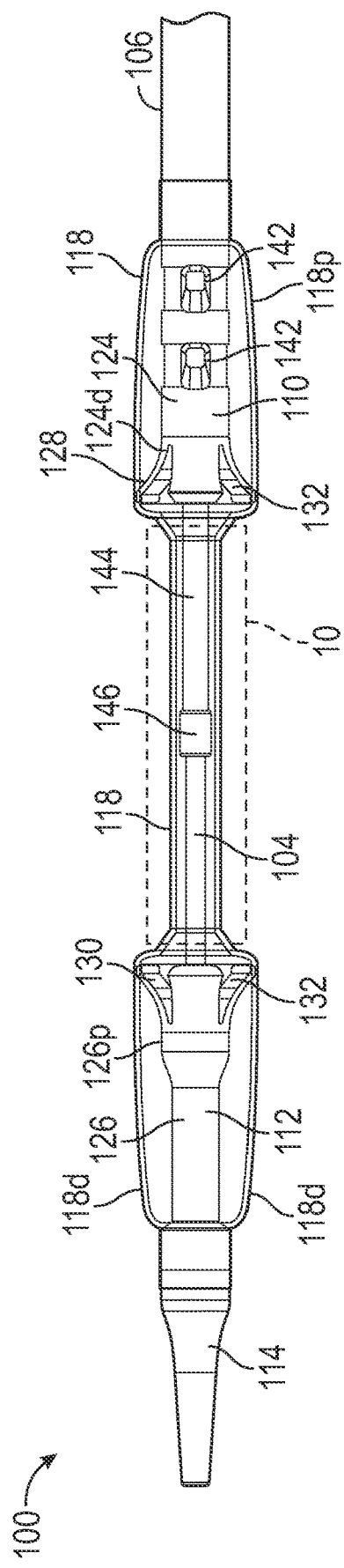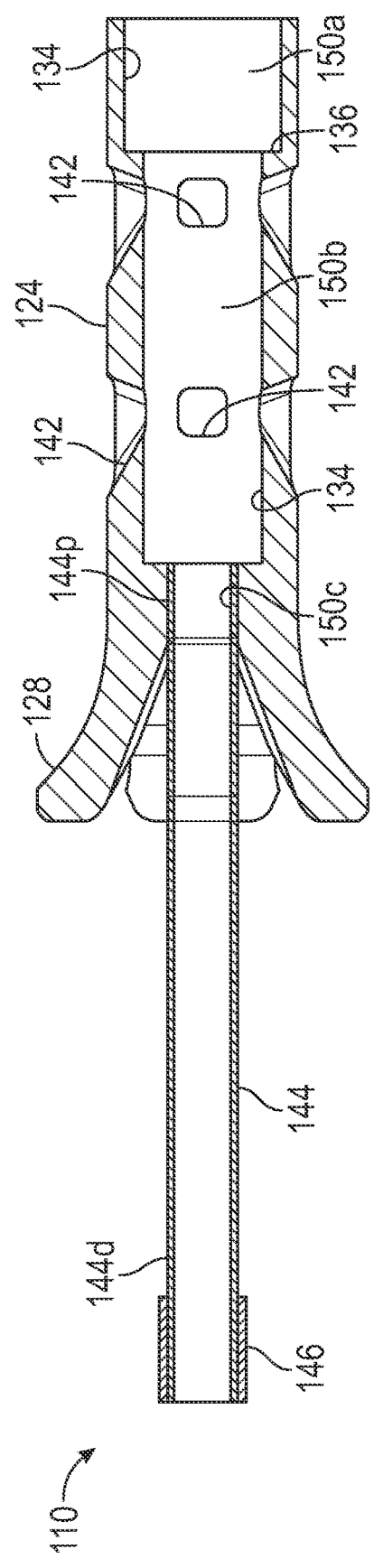

DELIVERY SYSTEMS FOR PROSTHETIC HEART VALVE

CROSS-REFERENCE TO RELATED APPLICATIONS

This application is a continuation of International Application No. PCT/US2019/064479 filed on Dec. 4, 2019, which claims the benefit of U.S. Provisional Application 62/778,159 filed on Dec. 11, 2018, both of which are incorporated by reference herein in its entirety.

FIELD

The present disclosure concerns embodiments of delivery systems for implanting prosthetic heart valves.

BACKGROUND

Prosthetic cardiac valves have been used for many years to treat cardiac valvular disorders. The native heart valves (such as the aortic, pulmonary and mitral valves) serve critical functions in assuring the forward flow of an adequate supply of blood through the cardiovascular system. These heart valves can be rendered less effective by congenital, inflammatory or infectious conditions. Such damage to the valves can result in serious cardiovascular compromise or death. For many years, the definitive treatment for such disorders was the surgical repair or replacement of the valve during open heart surgery, but such surgeries are prone to many complications. Because of the drawbacks associated with conventional open-heart surgery, percutaneous and minimally-invasive surgical approaches are garnering intense attention. In one technique, a prosthetic valve is configured to be implanted in a much less invasive procedure by way of catheterization.

In this technique, a prosthetic valve is mounted in a crimped state on the end portion of a flexible catheter and advanced through a blood vessel of the patient until the prosthetic valve reaches the implantation site. The prosthetic valve at the catheter tip is then expanded to its functional size at the site of the defective native valve such as by inflating a balloon on which the prosthetic valve is mounted. For instance, U.S. Pat. Nos. 5,411,522 and 6,730,118, which are incorporated herein by reference, describe collapsible transcatheter heart valves that can be percutaneously introduced in a compressed state on a catheter and expanded in the desired position by balloon inflation or by utilization of a self-expanding frame or stent.

A typical delivery apparatus for a transcatheter heart valve has a radiopaque marker that can be viewed under fluoroscopy. During delivery of the prosthetic valve, a physician can use the radiopaque marker to align the prosthetic valve with the implantation site. Using a conventional delivery apparatus, tension exerted on portions of the apparatus can result in the radiopaque marker being shifted relative to the prosthetic valve which can result in deployment of the prosthetic valve at the incorrect location.

Accordingly, a need exists for improved devices and methods for accurately determining a location of a prosthetic valve during an implantation procedure.

SUMMARY

Described herein are embodiments of a delivery assembly and method for implanting a prosthetic heart valve. The assembly can be used to precisely position a prosthetic valve at an implantation site within a patient.

In one representative embodiment, a delivery apparatus can include a handle, a first shaft extending from the handle, and a second shaft extending coaxially over the first shaft. The first and second shafts can have proximal end portions coupled to the handle and distal end portions. The delivery apparatus can further include a shoulder coupled to the distal end portion of the second shaft. The shoulder can have a flared end portion configured to abut a prosthetic valve positioned around the first shaft in a radially compressed state. The shoulder can further include an extension portion extending distally from the shoulder and at least one radiopaque marker disposed on the extension portion at a location within the prosthetic valve when the prosthetic valve is in a radially compressed configuration on the first shaft.

In some embodiments, the extension portion can be a tubular member, for example, a tubular member extending coaxially over the first shaft.

In some embodiments, the delivery apparatus further comprises a balloon disposed over the first shaft. In some embodiments, the shoulder can comprise an annular wall proximal to the flared portion. The annular wall can comprise one or more radially extending openings that allow an inflation fluid inside of the shoulder to flow outwardly through the one or more openings into the balloon.

In some embodiments, the shoulder can be a first shoulder and the delivery apparatus can further comprise a second shoulder coupled to the distal end portion of the first shaft. The first and second shoulders can be disposed within the balloon.

In some embodiments, the extension portion extends axially from a first location adjacent the first shoulder to a second location axially between the first and second shoulders. The second location can be about equidistant between the first and second shoulders.

In some embodiments, the at least one radiopaque marker comprises gold, platinum, radiopaque nitinol, and combinations thereof.

In another representative embodiment, a delivery assembly can include a balloon-expandable prosthetic heart valve radially expandable between a crimped configuration and an expanded configuration and a delivery apparatus. The delivery apparatus can comprise a handle, a first shaft extending from the handle, a second shaft extending from the handle coaxially over the first shaft, and a balloon. The first and second shafts can have proximal end portions coupled to the handle and distal end portions. The balloon can be disposed over the first shaft. The delivery apparatus can further comprise a proximal shoulder and a distal shoulder extending coaxially over the first shaft and disposed within the balloon. The proximal shoulder can include an extension portion extending from the proximal shoulder and at least one radiopaque marker on the extension portion. The prosthetic heart valve can be disposed on the balloon in the radially crimped configuration between the proximal and distal shoulders such that the at least one radiopaque marker is positioned within the prosthetic heart valve.

In some embodiments, the proximal shoulder can be coupled to a distal end portion of the second shaft and the distal shoulder can be coupled to a distal end portion of the first shaft.

In some embodiments, the at least one radiopaque marker can comprise gold, platinum, radiopaque nitinol, and combinations thereof.

In some embodiments, the first shaft can extend coaxially through the extension portion and is not secured directly to the extension portion. The extension portion can have a proximal end connected to the proximal shoulder and a distal end location axially between the proximal shoulder and the distal shoulder.

In another representative embodiment, a method of implanting a prosthetic heart valve, can comprise inserting a distal end portion of a delivery apparatus into the body of a patient. A balloon-expandable prosthetic heart valve can be coupled to the distal end portion of the delivery apparatus in a radially crimped configuration. The delivery apparatus can comprise a handle, a first shaft extending from the handle, and a second shaft extending from the handle over the first shaft. The delivery apparatus can further comprise a proximal shoulder extending over the first shaft, a distal shoulder extending over the first shaft, and a balloon disposed over the proximal and distal shoulders and the inner shaft. The proximal shoulder can include an extension portion extending from the proximal shoulder coaxially over the inner shaft having at least one radiopaque marker on the extension portion located within the prosthetic valve. The method can further include advancing the distal end portion of the delivery apparatus and the prosthetic valve distally through the vasculature of the patient to an implantation site, aligning the radiopaque marker with respect to the implantation site using fluoroscopy, and deploying the prosthetic valve to an expanded configuration at the implantation site.

In some embodiments, the implantation site can be a native aortic valve annulus of the patient's heart.

In some embodiments, the act of aligning the radiopaque marker with respect to the implantation site can comprise aligning the radiopaque marker with the native valve annulus.

The various innovations of this disclosure can be used in combination or separately. This summary is provided to introduce a selection of concepts in a simplified form that a further described below in the detailed description. This summary is not intended to identify key features or essential features of the claimed subject matter. The foregoing and other objects, features, and advantages of the disclosure will become more apparent from the following detailed description, which proceeds with reference to the accompanying figures.

BRIEF DESCRIPTION OF THE DRAWINGS

FIG. 3 is side elevation view of a distal end portion of the delivery apparatus of FIG. 2.

FIG. 4 is a cross-sectional view of a portion of the delivery apparatus of FIG. 2.

DETAILED DESCRIPTION

Described herein are systems and methods for delivering prosthetic devices, such as prosthetic heart valves, through the body and into the heart for implantation therein.

Prosthetic valves disclosed herein can be radially compressible and expandable between a radially compressed configuration and a radially expanded configuration. Thus, the prosthetic valves can be crimped on an implant delivery apparatus in the radially compressed configuration during delivery, and then expanded to the radially expanded configuration once the prosthetic valve reaches the implantation site.

Figure 1:
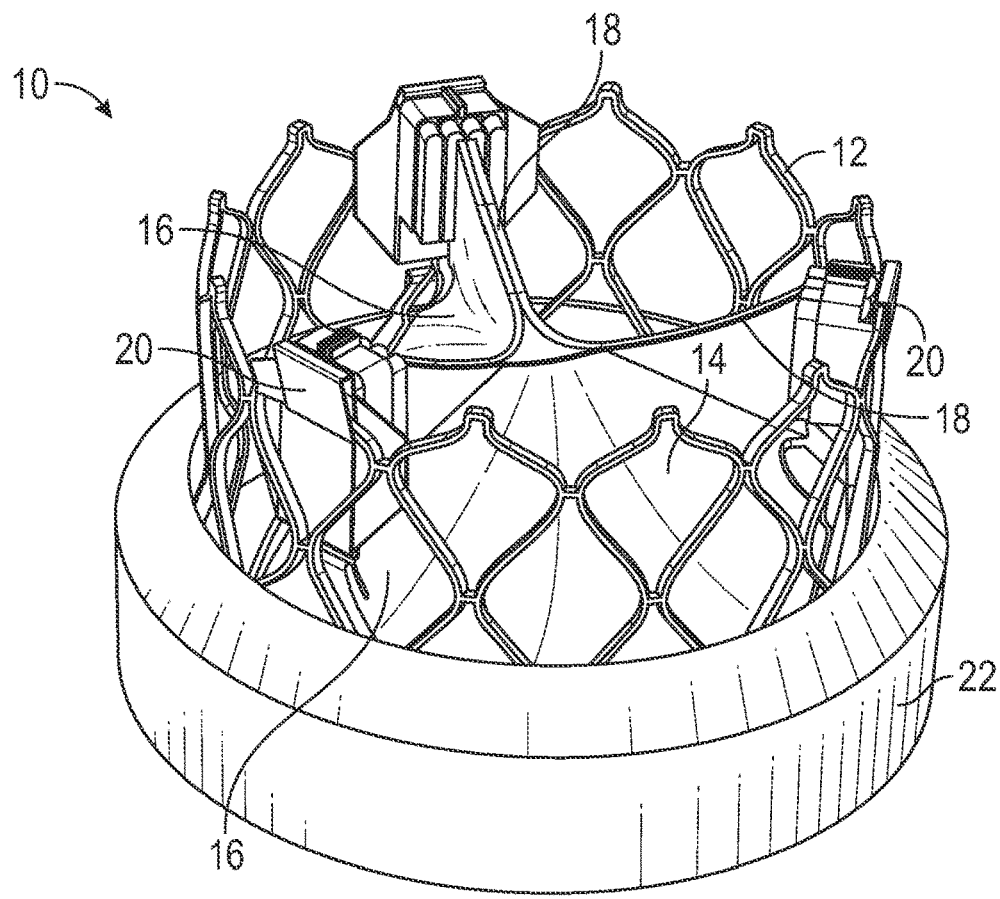
FIG. 1 is a perspective view of a representative embodiment of a prosthetic heart valve.

FIG. 1 shows an exemplary prosthetic valve 10, according to one embodiment. In particular embodiments, the prosthetic valve 10 can be implanted within the native aortic annulus, although it also can be implanted at other locations in the heart, including within the native mitral valve, the native pulmonary valve, and the native tricuspid valve. Prosthetic heart valve 10 comprises a stent or frame 12 and a valvular structure 14 supported by the frame and configured to regulate the flow of blood through the prosthetic valve.

In some embodiments, the prosthetic valve 10 is adapted to be implanted in the native aortic valve and can be implanted in the body using a delivery apparatus (see e.g., delivery apparatus 100 described below). The frame 12 can comprise a plastically expandable material, such as stainless steel, a nickel based alloy (e.g., a nickel-cobalt-chromium alloy), polymers, or combinations thereof, so that the frame 12 plastically expands when the prosthetic valve expands from the crimped, radially compressed configuration (FIG. 2) to the radially expanded configuration (FIG. 1) upon actuation of the delivery apparatus, for example, by inflating a balloon.

The valvular structure 14 can comprise plurality of leaflets 16 mounted inside of the frame. The opposing sides of each leaflet 16 can be paired with adjacent leaflets to form commissures 18 of the valvular structure. The commissures 18 can be mounted to the frame via reinforcing members 20. The prosthetic valve 10 can also include a sealing member 22 mounted on the outside of the frame. The sealing member 22 is configured to help seal the prosthetic valve against surrounding tissue and prevent or minimize perivalvular leakage. The leaflets 16 can be made from any of various suitable biocompatible materials, including natural tissue, such as bovine pericardial tissue (or pericardial tissue from other sources) or synthetic materials, such as any of various fabrics or non-fabric materials (e.g., polyurethane). The reinforcing members 20 and the sealing member 22 desirably are made of a fabric material, such as polyethylene terephthalate (PET) fabric, although non-fabric materials and natural tissue also could be used. Further details of the prosthetic valve 10 are disclosed in U.S. Patent Application Publication No. 2018/0028310, which is incorporated herein by reference. Other types of prosthetic heart valves that can deployed using any of the devices and methods disclosed herein are described in U.S. Pat. Nos. 7,510,575; 7,993,394; and 9,393,110, which are incorporated herein by reference.

Figure 2:
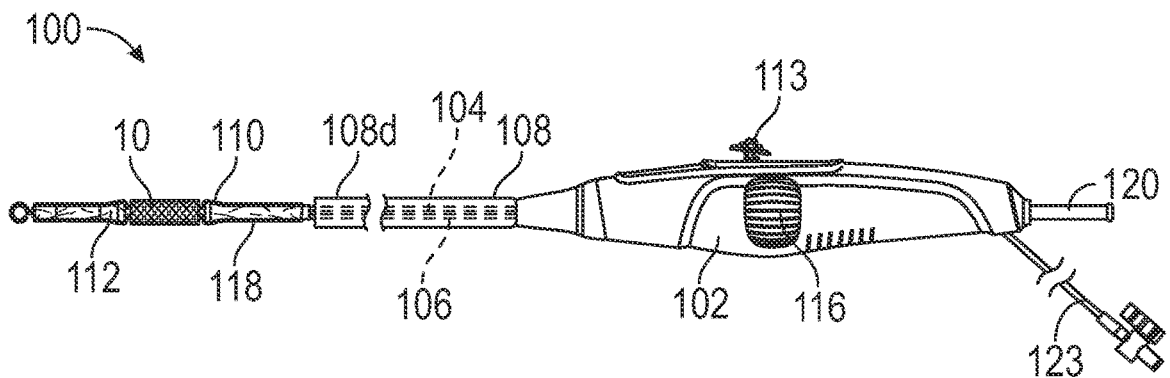
FIG. 2 is a side elevation view of a representative embodiment of a delivery apparatus for implanting a prosthetic heart valve.

FIG. 2 shows a delivery apparatus 100, according to one embodiment, adapted to deliver a prosthetic heart valve, such as the illustrated prosthetic heart valve 10. The prosthetic heart valve 10 can be, for example, a prosthetic aortic valve that is adapted to be implanted in the native aortic valve, although in other embodiments the prosthetic valve 10 can be implanted in any of the other native valves of the heart (the native mitral, tricuspid, or pulmonary valves).

The delivery apparatus 100 in the illustrated embodiment generally includes a handle 102, a first elongated shaft 104 extending distally from the handle 102, and a second shaft 106 extending co-axially over the first shaft 104, a third shaft 108 extending co-axially over the second shaft 106, one or more shoulders (e.g., a proximal shoulder 110 and a distal shoulder 112), and a nose cone 114 (see FIG. 3). In other embodiments, the delivery apparatus can include only a first shoulder (e.g., a proximal shoulder).

The first shaft 104 is the inner-most shaft in the illustrated embodiment and can be referred to as the inner shaft of the delivery apparatus 100. The second shaft 106 is the middle shaft in the illustrated embodiment and can be referred to as the intermediate shaft 106. Likewise, the third shaft 108 is the outer-most shaft 108 in the illustrated embodiment and can be referred to as the outer shaft or outer sheath of the delivery apparatus 100. The shafts 104, 106, 108 can be axially and/or rotationally movable relative to each other to facilitate delivery and positioning of the prosthetic valve 10 at an implantation site in the patient's body. The handle 102 can include one or more adjustment mechanisms configured to produce relative movement between the shafts. For example, the handle 102 can include a slideable adjustment lever 113 that is operatively connected to the second shaft 106. Thus, axial motion of the lever 113 can produce axial movement of the second shaft 106 (and, hence, of the prosthetic valve 10) in the proximal and distal directions relative to the first shaft 104.

The nose cone 114 (FIG. 3) can be connected to a distal end of the inner shaft 104. A guide wire (not shown) can extend through a central lumen of the inner shaft 104 and an inner lumen of nose cone 114 so that the delivery apparatus 100 can be advanced over the guide wire inside the patient's vasculature. The outer shaft 108 can also include a steerable portion 108*d*, the curvature of which can be adjusted by the operator to assist in guiding the apparatus through the patient's vasculature and, in particular, the aortic arch. The steerable portion 108*d* can be coupled to a control device (e.g., knob 116) by at least one pull wire, such that tensioning and releasing the pull wire causes corresponding flexing and unflexing of the steerable section 108*d* of the outer shaft 108 and therefore of the first and second shafts 104, 106. Further details regarding the steering of the delivery apparatus are described in U.S. Patent Application Publication 2017/0065415, which is incorporated herein by reference.

The proximal ends of the shafts 104, 106, 108 can be coupled to the handle 102. During delivery of a prosthetic valve, the handle 102 can be maneuvered by a physician to advance or retract the delivery apparatus through the patient's vasculature. In some embodiments, the handle 102 can include one or more adjustment mechanisms, for example, knob 116 and lever 113, or other actuating mechanisms for controlling different components of the delivery apparatus 100 in order to expand and/or deploy the prosthetic valve.

The shafts 104, 106, 108 can be formed from any of various suitable materials and techniques, such as any of various polymers, including nylon, or a polyether block amide (commercially available as Pebax®), which can be extruded to form the shafts. In other examples, any of the shafts 104, 106, 108 can comprise a braided layer formed from metal (e.g., Nitinol or stainless steel) or polymeric wires, or a combination of a one or more braided layers and one or more extruded polymeric layers. The shafts can have longitudinal sections formed from different materials in order to vary the flexibility of the shafts along their lengths. The first shaft 104 can have an inner liner or layer formed of a low friction material, such as polytetrafluoroethylene (commercially available as Teflon®) to minimize sliding friction with a guide wire.

An inflatable balloon 118 can be mounted along the distal end portions of the first and second shafts 104, 106 and can extend over the proximal and distal shoulders 110, 112. As best shown in FIG. 3, the balloon 118 has a proximal end portion 118*p* that can be secured to the outer surface of the second shaft 106 and a distal end portion 118*d* that can be secured to the outer surface of the nose cone 114 or the outer surface of the distal shoulder 112. As depicted in FIG. 2, the prosthetic valve 10 can be radially crimped between the shoulders 110, 112 over the balloon 118 for delivery into a patient's vasculature. Once the prosthetic valve 100 reaches the desired implantation site (e.g., within the native aortic valve), the balloon 118 can be inflated to radially expand the prosthetic valve against the surrounding tissue, as described in more detail below.

The delivery apparatus 100 can include a proximal port 120 extending from the handle 102. The first and second shafts 104, 106 can be sized such that a first annular space 122 (see FIG. 5) is defined between the first and second shafts 104, 106 along the entire length of the second shaft 106. In use, the proximal port 120 can be fluidly connected to a fluid conduit (e.g., tubing), which in turn can be fluidly connected to a fluid source (e.g., a syringe containing an inflation fluid, such as saline) to inflate the balloon 118. Thus, the fluid conduit can be in fluid communication with the first annular space 122 between the first and second shafts 104, 106 such that fluid can flow through the delivery apparatus and inflate the balloon 118, as described in more detail below. The handle 102 can further include a side arm 123 which can be, for example, a flush tube having an internal passage that fluidly communicates with the first annular space 122.

Further details regarding the delivery apparatus 100 and methods for delivering and deploying a prosthetic valve using the delivery apparatus can be found, for example, in U.S. Publication No. 2017/0065415. Other examples of delivery apparatuses that can be used to implant a prosthetic heart valve with devices disclosed herein are described in U.S. Patent Publication No. 2009/0281619, incorporated herein by reference.

Referring now to FIG. 3, as noted above, the delivery apparatus can comprise one or more shoulders. In the illustrated embodiment, the delivery apparatus 100 includes a proximal shoulder 110 and a distal shoulder 112. In other embodiments, the delivery apparatus can include only a single shoulder, for example, proximal shoulder 110.

The distal shoulder 112 can be connected to a distal end portion of the first or inner shaft 104 and/or the nose cone 114. In some embodiments, the nose cone 114 and the distal shoulder 112 can be integrally formed as a single component. In other embodiments, the nose cone 114 and the distal shoulder 112 can be separately formed and connected to each other during the process of assembling the delivery apparatus. In other embodiments, the nose cone 114 and the distal shoulder 112 can be spaced apart from each other along the first shaft 104. The proximal shoulder 110 can be connected to a distal end portion 106*d* (FIG. 5) of the second shaft 106. The proximal and distal shoulders 110, 112 can be disposed within the balloon 118.

Each shoulder 110, 112 can comprise a body 124, 126, respectively. In some embodiments, each shoulder can further comprise a flared end portion 128, 130, respectively. The flared end portion 130 of the distal shoulder 112 can be located at a proximal end portion 126*p* of the body 126, and the flared end portion 128 of the proximal shoulder 110 can be located at a distal end portion 124*d* of the body 124. Each flared end portion 128, 130 can have a diameter equal to or slightly greater than a diameter of the prosthetic valve 10 when in the compressed or crimped configuration on the balloon 118. The flared end portions 128, 130 of the shoulders 110, 112 can define a space sized to at least partially receive the prosthetic valve 10 when it is crimped on the balloon 118. In this way, the flared end portions 128, 130 help restrain the prosthetic valve 10 against movement relative to the delivery apparatus 100 during the implantation procedure.

The flared end portions 128, 130 can each comprise one or more slots 132. In the illustrated embodiment, each flared end portion comprises four slots 132 that are equally spaced circumferentially about the flared end portion. However, other embodiments can comprise a greater or fewer number of slots. The slots 132 facilitate radial compression of the flared end portions 128, 130, which is advantageous during manufacturing of the delivery apparatus and during crimping of the prosthetic valve 10. The flared end portions 128, 130 can be radially compressed to a smaller diameter using slots 132 for insertion into the balloon 118 and then allowed to expand once inside the balloon 118. In addition, the slots 132 can facilitate the flow of fluid through the balloon 118, as discussed in more detail below. Further details regarding the shoulders of the delivery apparatus and methods for delivering and deploying a prosthetic valve using the delivery apparatus can be found, for example, in U.S. Publication Nos. 2013/0030519 and 2017/0065415, which are incorporated herein by reference in its entirety.

Referring now to FIG. 4, the body 124 of the proximal shoulder 110 can have an annular shape defining an inner lumen. The inner lumen of the proximal shoulder 110 can be formed with a stepped surface 134 extending through the proximal shoulder 110. The stepped surface 134 can be formed with a first annular lip 136 and a second annular lip 138, so as to define a proximal lumen portion 150*a*, an intermediate lumen portion 150*b*, and a distal lumen portion 150*c*.

Figure 5:
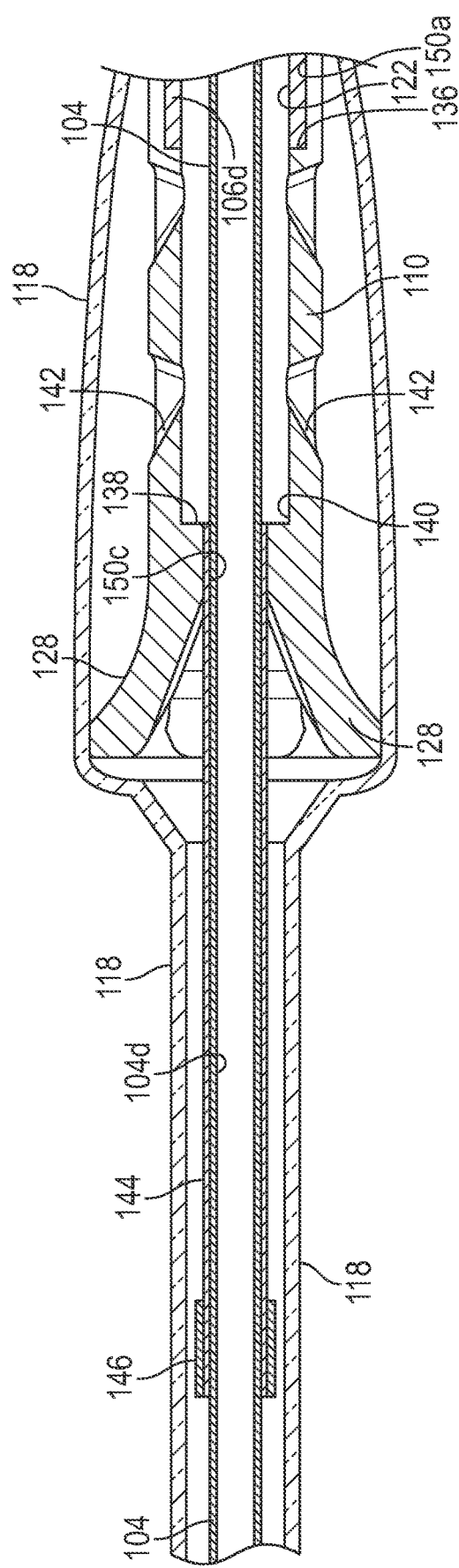
FIG. 5 is a partial cross-sectional view of the delivery apparatus of FIG. 2.

Referring now to FIG. 5, the distal end portion 106*d* of the second shaft 106 extends partially into the proximal lumen portion 150*a* and abuts the first annular lip 136. The distal end portion 106*d* of the second shaft 106 can be fixedly secured within the proximal shoulder 110, such as with an adhesive, welding, and/or a friction or interference fit. The distal lumen portion 150*c* can be sized such that the first shaft 104 can extend therethrough. The intermediate lumen portion 150*b* and the first shaft 104 can be sized such that a second annular space 140 is defined radially between the outer surface of the first shaft 104 and the inner surface of the body 124 and axially between the first annular lip 136 and the second annular lip 138. The second annular space 140 is in fluid communication with the first annular space 122 such that an inflation fluid can flow through the first annular space 122 into the second annular space 140.

The proximal shoulder 110 can comprise one or more openings 142 formed in the annular wall between the outer and inner surfaces of the proximal shoulder 110. The openings 142 can be in fluid communication with the second annular space 140 such that an inflation fluid can flow from the second annular space 140 outwardly through the openings 142 and into the balloon 118. For example, an inflation fluid from the fluid source can flow through the fluid conduit, through the first annular space 122, through the second annular space 140, outwardly through the openings 142, and into the balloon 118 to inflate the balloon and deploy the prosthetic valve 10. The slots 132 in the flared end portions 128, 130 of the shoulders 110, 112 facilitate the flow of inflation fluid distally through the flared end portion 128 of the proximal shoulder, through the region of the balloon 118 extending through the prosthetic valve 10, through the flared end portion 130 of the distal shoulder 112, and into a distal region of the balloon 118*d* (FIG. 3), thus facilitating even expansion of the balloon 118.

Referring again to FIG. 4, the proximal shoulder 110 can further comprise an extension portion 144. The extension portion 144 can extend distally from the body 124 of the proximal shoulder 110. The extension portion 144 can be, for example, a tubular member or shaft extending over a distal end portion 104*d* of the first shaft 104 (FIG. 5). The extension portion 144 can have a proximal end portion 144*p* that extends into the distal lumen portion 150*c* of the proximal shoulder and is fixedly secured therein.

In the illustrated embodiment, the extension portion 144 has a cylindrical shape and a circular cross-sectional profile in a plane perpendicular to the longitudinal axis of the delivery apparatus. In other examples, the extension portion can have any of various other shapes. For example, the extension portion 144 can have a cross-sectional shape in a plane perpendicular to the longitudinal axis of the delivery apparatus that does not extend completely around the first shaft 104, such as a C-shape. In another implementation, the extension portion can be a relatively flat component, such as beam-like component having a rectangular or square shaped cross-sectional profile, and can extend along one side of the first shaft 104.

In some embodiments, the extension portion 144 can extend from the proximal shoulder 110 at least a length equal to half the length of the prosthetic valve 10 when in the compressed configuration. The extension portion 144 can be formed from any of various suitable materials, for example, the extension portion 144 can be formed from a polymer (nylon or Pebax) such that chafing or scoring between extension portion 144 and the first shaft 104 is mitigated.

In the illustrated embodiment, the extension portion 144 is fixedly secured to the proximal shoulder 110 by overmolding the proximal shoulder 110 onto an end portion, for example the proximal end portion 144*p*, of the extension portion 144. In other embodiments, the end portion 144*p* can be fixedly secured within the distal lumen portion 150*c* of the proximal shoulder 110 using, for example, an adhesive, welding, and/or an interference fit. In other embodiments, the extension portion 144 can be fixedly secured to the proximal shoulder without extending into the distal lumen portion 150*c*.

In alternative embodiments, the extension portion 144 can be integrally formed as part of the proximal shoulder 110, meaning that the extension portion 144 and the proximal shoulder have a one-piece, unitary construction without any fasteners, welds, or adhesives securing the extension portion 144 to the proximal shoulder 110. For example, the proximal shoulder 110 can be formed by a molding process (e.g., injection molding) wherein the extension portion 144 is formed as part of the proximal shoulder 110 during the molding process.

The extension portion 144 can comprise at least one radiopaque marker 146. The radiopaque marker 146 can be disposed on the extension portion 144 at a location within the prosthetic valve 10 when the prosthetic valve 10 is in a radially compressed configuration between the proximal and distal shoulders 110, 112. For example, the radiopaque marker 146 can be disposed on, or extend from a distal end portion 144*d* of the extension portion 144.

In a conventional delivery apparatus, the radiopaque marker typically is disposed on the innermost shaft extending through the balloon. As a result, any movement of the innermost shaft relative to the prosthetic valve, such as may be caused by compression or deflection of the innermost shaft as the delivery apparatus is steered around the aortic arch, can displace the radiopaque marker from its intended position within the prosthetic valve, which can inhibit precise alignment of the prosthetic valve at the intended deployment location.

However, in the illustrated embodiment, the radiopaque marker 146 has a fixed position relative to the proximal shoulder 110 by virtue of the extension portion 144. The extension portion 144 desirably is not fixed to the distal end portion 104d of the first shaft and therefore the distal end portion 104d is able to move relative to the proximal shoulder 110 if the distal end portion undergoes compression or deflection. Any movement of the distal end portion 104d of the first shaft 104 therefore does not result in movement of the marker 146 relative to the proximal shoulder 110 and the prosthetic valve 10. Therefore, by placing the radiopaque marker 146 on the extension portion 144, the physician can position the prosthetic valve 10 at a selected implantation location within the patient, for example, the native aortic annulus, with much greater precision and accuracy compared with known delivery apparatuses.

In the illustrated embodiment, the radiopaque marker 146 is a marker band extending annularly around a distal end portion 144d of the extension portion 144. In other embodiments, the radiopaque marker can be a series of radiopaque bands or a radiopaque pattern and can be disposed along the length of the extension portion 144 (e.g., spaced apart from each other along the length of the extension portion 144)). Also, the radiopaque markers need not be annular bands that extend completely around the extension portion 144. Instead, the radiopaque markers can comprise any of various shapes, such as partial bands, or axially extending lines. In still other embodiments, the radiopaque marker can extend from the distal end portion 144d of the extension portion 144. The radiopaque marker 146 can comprise, for example, gold, platinum, radiopaque nitinol, and combinations thereof.

In other embodiments, in lieu of or in addition to the radiopaque marker 146, the extension portion 144 itself can comprise a radiopaque material such as gold, platinum, radiopaque nitinol, or combinations thereof. Some or all of the extension portion 144 can be formed from radiopaque material. In such embodiments, the distal end of the extension portion 144 can be used to position the prosthetic valve 10 at the selected implantation location within the patient.

The delivery apparatus 100 can be used to deliver and implant a prosthetic heart valve, for example, prosthetic heart valve 10, in the following exemplary manner. The prosthetic valve 10 can be crimped on the distal end portion of delivery apparatus 100, between the proximal and distal shoulders 110, 112 such that extension portion 144 comprising marker band 146 is disposed within the prosthetic valve 10. The distal end of delivery apparatus 100 (along with prosthetic valve 10) can be advanced through the vasculature of a patient to a selected implantation site (e.g., the native aortic annulus). A physician can use the radiopaque marker 146 to align the prosthetic valve with the implantation site, for example, by visualizing the marker 146 using fluoroscopy.

Once the physician has determined that the prosthetic valve 10 is positioned as desired at the implantation site, the prosthetic valve 10 can be deployed (e.g., radially expanded). To deploy the prosthetic valve, an inflation fluid from a source (e.g., a syringe) is introduced under pressure into the first annular space 122 through the length of the second shaft 106, through the second annular space 140, out the openings 142, and into the balloon 118, thus inflating the balloon 118 and expanding the prosthetic valve 10 so as to contact the native annulus. Other examples of methods for implanting a prosthetic valve can be found, for example, in U.S. Publication No. 2017/0065415.

As mentioned above, the length of the extension portion 144 in the illustrated embodiment is selected such that the marker 146 is at the middle or mid-section of the prosthetic valve 10 (halfway between the inflow and outflow ends of the prosthetic valve) during delivery. In this manner, the marker 146 can be used to align the mid-section of the prosthetic valve with a particular location or area of the patient's anatomy. In other embodiments, the extension portion 144 can have different lengths and the marker 146 can be at another location within the prosthetic valve, such as at the inflow end or the outflow end of the prosthetic valve, to enable alignment of another section of the prosthetic valve with a particular location or area of the patient's anatomy. In one specific implementation, the extension portion 144 can extend the entire length between the proximal and distal shoulders 110, 112 and one or more markers 146 can be positioned at selected locations along the length of the extension portion 144, such as at locations corresponding to the inflow end, mid-section, and outflow end of the prosthetic valve.

As noted above, the stationary position of the radiopaque marker 146 with respect to the proximal shoulder 110 prevents the marker from being shifted from its intended location relative to the prosthetic valve 10, thus allowing the prosthetic valve 10 to be precisely positioned within the native annulus without interference caused by the movement of the first shaft 104 relative to the proximal shoulder 110.

General Considerations

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

All features described herein are independent of one another and, except where structurally impossible, can be used in combination with any other feature described herein.

As used in this application and in the claims, the singular forms "a," "an," and "the" include the plural forms unless the context clearly dictates otherwise. Additionally, the term "includes" means "comprises." Further, the terms "coupled"

and "associated" generally mean electrically, electromagnetically, and/or physically (e.g., mechanically or chemically) coupled or linked and does not exclude the presence of intermediate elements between the coupled or associated items absent specific contrary language.

In the context of the present application, the terms "lower" and "upper" are used interchangeably with the terms "inflow" and "outflow", respectively. Thus, for example, the lower end of the valve is its inflow end and the upper end of the valve is its outflow end.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

In view of the many possible embodiments to which the principles of the disclosure may be applied, it should be recognized that the illustrated embodiments are only preferred examples and should not be taken as limiting the scope of the disclosure. Rather, the scope of the disclosure is defined by the following claims.

We claim:

1. A delivery apparatus, comprising:
   a handle;
   a first annular shaft extending from the handle, the first shaft having a proximal end portion coupled to the handle and a distal end portion, wherein the first shaft has a lumen for receiving a guidewire;
   a second annular shaft extending coaxially over the first shaft and having a proximal end portion coupled to the handle and a distal end portion;
   a shoulder coupled to the distal end portion of the second shaft, the shoulder having a flared end portion configured to abut a prosthetic valve positioned around the first shaft in a radially compressed state;
   an extension portion extending distally from the shoulder, the extension portion having a proximal end and a distal end, wherein the proximal end is connected to the shoulder; and
   at least one radiopaque marker disposed on the extension portion at a location within the prosthetic valve when the prosthetic valve is in a radially compressed configuration on the first shaft.

2. The delivery apparatus of claim 1, wherein the extension portion is a tubular member.

3. The delivery apparatus of claim 2, wherein the tubular member extends coaxially over the first shaft.

4. The delivery apparatus of claim 3, further comprising a balloon disposed over the first shaft, wherein the distal end of the extension portion is positioned inside of the balloon proximal to a distal end of the balloon.

5. The delivery apparatus of claim 4, wherein the shoulder comprises an annular wall proximal to the flared end portion, the annular wall comprising one or more radially extending openings that allow an inflation fluid inside the shoulder to flow outwardly through the one or more openings into the balloon.

6. The delivery apparatus of claim 5, wherein the shoulder is a first shoulder and the delivery apparatus further comprises a second shoulder mounted on the distal end portion of the first shaft.

7. The delivery apparatus of claim 6, wherein the first and second shoulders are disposed within the balloon.

8. The delivery apparatus of claim 6, wherein the extension portion extends axially from a first location adjacent the first shoulder to a second location axially between the first and second shoulders.

9. The delivery apparatus of claim 8, wherein the second location is about equidistant between the first and second shoulders.

10. The delivery apparatus of claim 4, further comprising a nose cone connected to the distal end portion of the first shaft, wherein the nose cone extends distally of a distal end of the balloon.

11. The delivery apparatus of claim 1, wherein the at least one radiopaque marker comprises one or more of gold, platinum, and radiopaque nitinol.

12. The delivery apparatus of claim 1, wherein the flared end portion comprises one or more slots configured to facilitate radial compression of the flared end portion.

* * * * *